United States Patent [19]
Sandig et al.

[11] Patent Number: 6,025,195
[45] Date of Patent: Feb. 15, 2000

[54] LIVER-SPECIFIC ADENOVIRUS EXPRESSION VECTOR

[75] Inventors: Volker Sandig; Peter Löser; Michael Strauss, all of Berlin, Germany

[73] Assignee: Max-Planck-Gesellschaft zur Förderung der Wissenschaften E.V. Berlin, Germany

[21] Appl. No.: 08/983,099

[22] PCT Filed: Jul. 8, 1996

[86] PCT No.: PCT/DE96/01253

§ 371 Date: Apr. 23, 1998

§ 102(e) Date: Apr. 23, 1998

[87] PCT Pub. No.: WO97/04117

PCT Pub. Date: Feb. 6, 1997

[30] Foreign Application Priority Data

Jul. 15, 1995 [DE] Germany ............... 195 25 900

[51] Int. Cl.⁷ ............... C12N 15/86; C07H 21/04
[52] U.S. Cl. ............... 435/320.1; 536/23.5; 536/24.1
[58] Field of Search ............... 435/69.1, 320.1, 435/455, 456; 424/93.1, 93.2, 93.6; 536/23.1, 23.5, 24.1

[56] References Cited

U.S. PATENT DOCUMENTS 5,895,759   4/1999   Strauss et al. ............... 435/320.1

FOREIGN PATENT DOCUMENTS 43 39 922   10/1994   Germany.
WO 94/10322   5/1994   WIPO.
WO 95 16772   6/1995   WIPO.

OTHER PUBLICATIONS

Chen et al., J. Virol., vol. 66, No. 12, pp. 7452–7460. Dec. 1992.

*Primary Examiner*—David Guzo
*Attorney, Agent, or Firm*—Londa and Traub LLP

[57] ABSTRACT

The invention concerns an adenovirus vector for liver specific gene therapy; fields of application in medicine are the treatment of gene defects and tumour diseases of the liver and molecular biology. The vector according to the invention is marked by the fact that a therapeutic gene is coupled with a liver-specific promoter consisting of enhancer elements of the hepatitis B virus and an enhancerless minimum promoter and is optionally surrounded by SAR elements wherein the promoter is inserted into the adenovirus genome.

10 Claims, 5 Drawing Sheets

| cell type/plasmid | HepG2 | | HuH7 | | HepSV40 | | NIH 3T3 | | HeLa | | CV-1 | |
|---|---|---|---|---|---|---|---|---|---|---|---|---|
| pCMVluc | 100 | | 100 | | 100 | | 100 | | 100 | | 100 | |
| pSV2luc | 12.9 | (1.4) | 9.6 | (1.8) | n.d. | | 12.5 | (2.7) | 8.1 | (0.5) | n.d. | |
| pCPluc | 5.4 | (1.7) | 4.7 | (0.2) | 1.5 | (0.4) | 0.2 | (0.03) | 0.2 | (0.01) | 0.3 | (0.04) |
| pSCPluc | 4.2 | (0.9) | 5.1 | (0.6) | 0.8 | (0.2) | 0.2 | (0.02) | 0.6 | (0.1) | n.d. | |
| pECPluc | 15.7 | (3.7) | 10.2 | (1.6) | 9.4 | (1.0) | 0.7 | (0.08) | 0.7 | (0.2) | 0.9 | (0.2) |
| pXPluc | 5.7 | (1.2) | 1.2 | (0.2) | 22.4 | (5.6) | 2.8 | (0.4) | n.d. | | 5.9 | (0.4) |
| pSPluc | 1.1 | (0.4) | 2.1 | (0.3) | 1.3 | (0.1) | 0.04 | (0.01) | 0.01 | (0.003) | n.d. | |

FIG. 1

LIVER-SPECIFIC ADENOVIRUS EXPRESSION VECTOR

CROSS-REFERENCES TO RELATED APPLICATIONS

This application is a United States national stage of PCT/DE96/01253, filed Jul. 8, 1996.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

The invention relates to an adenovirus vector for liver-specific gene therapy. Fields of application include medicine, the treatment of gene defects and tumour diseases of the liver, and molecular biology.

Numerous methods and vectors for gene therapy have been developed in recent years (survey in Mulligan/1993/Science 260, 920). Vectors derived from viruses are compared with those from non-viral transfer methods where the therapeutic gene is embedded in protein or lipid coats. The particles derived from the non-viral methods can preferentially bind to specific receptors once the particles are coupled to ligands for these receptors. This specificity works as an advantage to the gene therapeutic system in vivo. However, the therapeutic gene reaches only the tissue where its activity is desired.

Yet, viral vectors, notably the virus groups retrovirus and adenovirus have shown a higher efficiency in vivo. Both viruses allow the transfer of genes in liver cells. The retroviral infection leads to a stable integration of the genetic material into the cellular genome. This process depends on the proliferation of cells—a rare event for liver cells in vivo. Hepatocytes in culture are infected with retroviruses sufficiently. In the liver, however, either a partial liver resection is necessary to stimulate cell division (Ferry et al./1991/Proc. Natl. Acad. Sci. USA 88, 8377) or the application of methods which result in an acute decrease in the number of hepatocytes (Lieber et al. Proc. Natl. Acad. Sci. USA in press) is required to produce the same results.

Adenoviruses are by far more superior and more efficient to all other types of vectors. Even if administered intravenously, the virus may reach nearly 100 percent of the hepatocytes. Adenoviruses are available as episomes in the cell.

In contrast to retrovirus vectors, adenoviral vectors contain the biggest part of the viral genome. Originally, only the E1 region was transferred to the helper cell (HEK293) and used for the multiplication of viruses, thus preventing the virus from being replicated in the target tissue. As the adenovirus coat may receive up to 105 percent of the size of a genome (40 kb) the deletion of E1 was also essential for the insertion of new genes. To increase the capacity to a maximum of 8.3 kb, parts of the E3 region were additionally deleted (Bett et al./1994/Proc. Natl. Acad. Sci. USA 91, 8802). Although the most important transactivators of adenoviral genes—products of the E1 region—are lacking, other viral genes are expressed in addition to the therapeutic gene. The exposition of the respective proteins on the cell surface results in an activation of CD8 positive T-cells and an elimination of the infected cells. By eliminating further transactivators, e.g. E2A, it was functionally possible to reduce this effect farther (Yang et al./1994/Nature Genetics 7, 362).

An essential drawback of the existing adenovirus vectors is the lack of tissue specificity. Adenovirus receptors exist in a multitude of cell types, thereby explaining the lack of enthusiasm for methods calling for the additional coupling of the virus with ligands of specific receptors.

Liver specificity may also be achieved by using liver-specific promoters apart from the reception mode. Various cellular promoters (albumin and alpha1 antitrypsin promoters) active in hepatocytes were examined for gene therapy in retroviruses (Rettinger et al./1994/Proc. Natl. Acad. Sci. USA 91, 1460). Their size, however, makes them unsuitable in adenovirus vectors. Furthermore, the strong viral promoters (CMV and RSV promoters), frequently applied in the adenoviral context, are ubiquitously active and eliminated in the liver after a short time.

BRIEF SUMMARY OF THE INVENTION

This invention is aimed at constructing a vector that combines the advantages of an adenovirus vector with the property of liver-specific expression of therapeutic genes.

BRIEF DESCRIPTION OF THE SEVERAL VIEWS OF THE DRAWINGS

FIG. 1 Expression of the luciferase reporter gene controlled by various promoters in hepatocyte cell lines and cell lines of a different origin, measured as activity of the luciferase encyme.

The activity is given as percent (%) of the activity achieved with the CMV promoter. The values given are averages from 4 independent transfection experiments.

Figure 2:
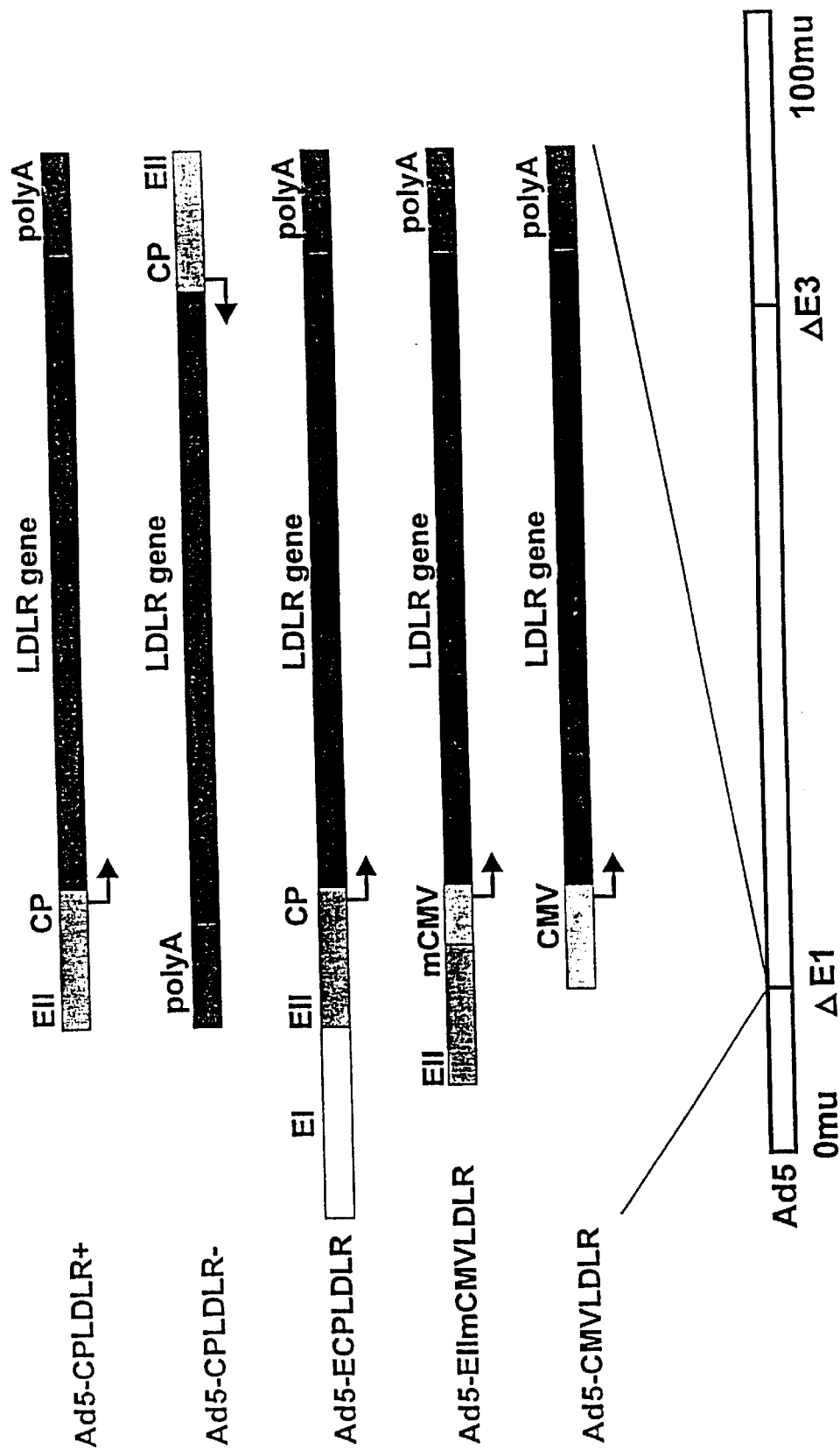

FIG. 2 Construction of adenoviruses expressing the gene of the human LDL receptor under the control of promoters derived from CMV or HBV.

CMV, CMV immediate early promoter; CP, HBV core promoter; EI, EBC enhancer I; EII, HBV enhancer II; mCMV, minimum CMV promoter; polyA; polyadenylation signal of the bovine growth hormone FIG. 3 Expression of LDL receptors in cell lines after an adenoviral gene transfer FIG. 4 (Parts A–C Expression of the human receptor gene in vivo Samples of the respective tissue were powdered and used in equal amounts for isolating RNA and genomic DNA. Ten (10) µg of the total RNA were always used in the RNA protection assay. Here, an anti-sense RNA of the LDL receptor organ or the GAPDH gene synthesised in vitro by means of T7 RNA polymerase using $^{32}$p-marked nucleotides serves as a sample. It is protected against RNAse digestion over a length of 304 bp (LDLR) or 316 bp (GAPDH) of the respective cellular transcript.

Genomic DNA was analysed using Southern Blotting for analysing the efficiency of infection. Ten (10) µg of genomic DNA were digested with Nco1 and separated in agarose gel. In this connection, a 1584 bp long fragment will be released in the 5' region of the adenovirus which will be detected by hybridisation by means of a $^{32}$marked DNA probe (equal fragment).

Figure 5:
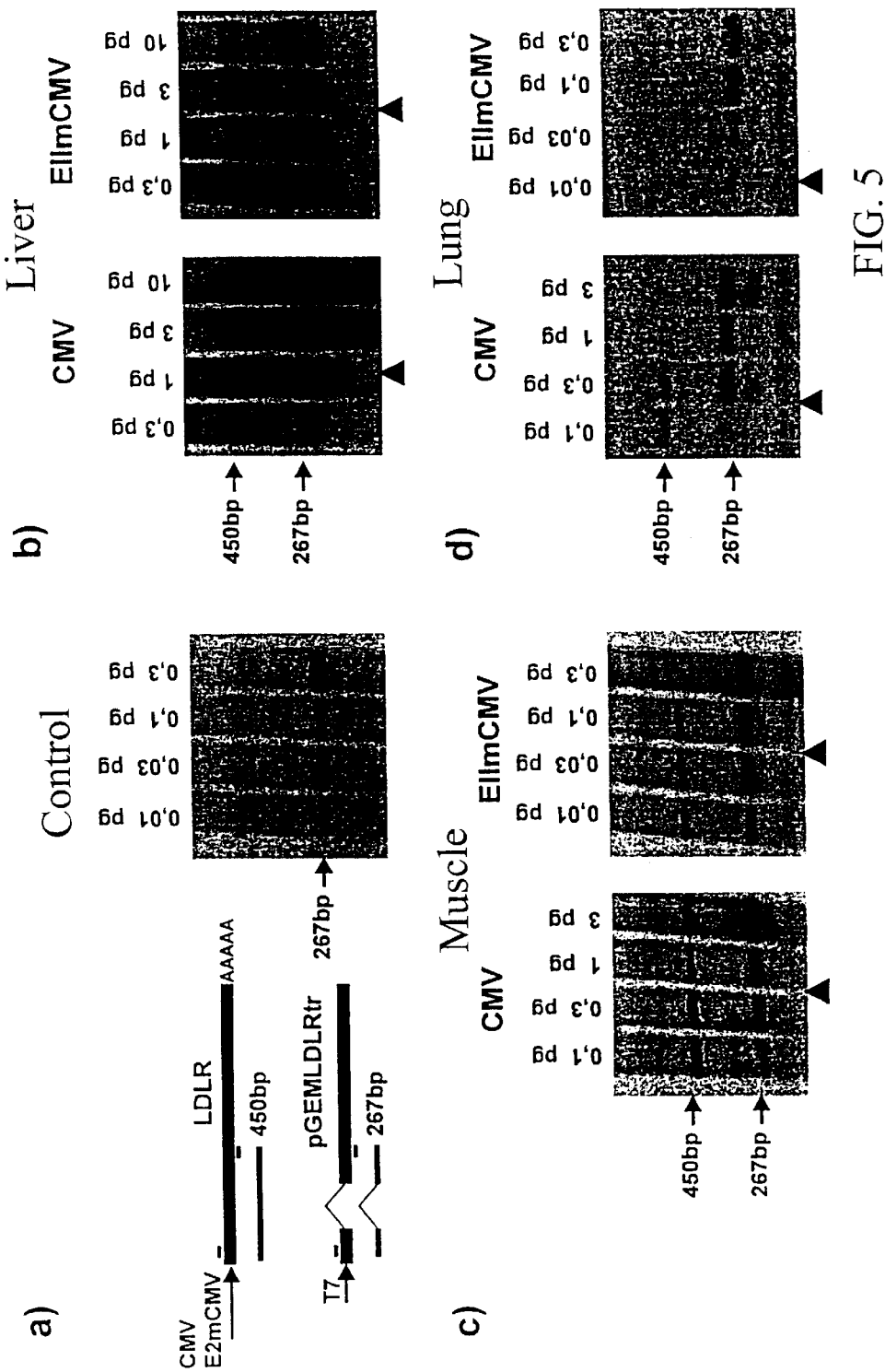

FIG. 5 (Parts A–D) Expression of the human LDL receptor gene in vivo by means of RT-PCR a) Schematic representation of the principle of the competitive RT-PCR. When amplifying a LDLR-RNA transcribed in reverse order from the tissue a 450 bp long fragment is obtained. A 267 bp long fragment is amplified from the shortened LDLR-RNA synthesised in vitro after reverse transcription.

b,c,d) Equal quantities of RNA from the respective tissue were mixed with increasing quantities of the shortened transcript, transcribed in reverse order and subjected to a PCR by $^{32}$marked nucleotides over 30 cycles. After having been separated in agarose gel on the phosphoimmager (Fuji) the PCR products were analysed.

The triangles show the mixing ratio where PCR products are available in equivalent quantities.

DETAILED DESCRIPTION OF THE INVENTION

An essential component of the invention is a short, highly active and liver-specific promoter which is coupled to the therapeutic gene. It consists of enhancer elements of the hepatitis B virus and an enhancerless minimum promoter. Moreover, it is necessary to surround the promoter with SAR elements (scaffold attached regions), in order to protect the inserted gene against the effects of adenoviral enhancers. The SAR region of the human interferon-β-gene is preferentially used as such an element.

Enhancer II of the hepatitis B virus (subtype ayw) is preferentially used as an enhancer element. It is detected by positions 1628–1807 on the viral gene.

A part of the former promoter of the cytomegalovirus is used as the enhancerless minimum promoter. It is located at positions −55 to +69 with respect to the start of transcription. Essential elements of the minimum promoter are the TATA box, the "cap place" and the 5'-non-translated region. The minimum promoter has a low basic expression and may be activated by enhancer II of the hepatitis B virus.

According to the invention, the preferential place for the insertion of the expression unit consisting of the enhancer, promoter and gene is region E1 of the adenogenome. Notably, subtypes 2 and 5 of this virus are used as adenoviruses.

The cDNA of the human LDL receptor is used as the therapeutic gene. The receptor is normally expressed at a high rate in hepatocytes. In patients with the disease family hypercholesterolaemia this gene is mutated. The therapy requires a high expression of the receptor as well as a lasting effect in these cells.

The cDNAs of other genes may replace or substitute the cDNA of the LDL receptor if these genes are defective in the disease to be cured, and they are mainly active in the liver.

The advantages of the vector in conformity with the invention are the high efficiency of the infection combined with a high specificity of expression in liver cells. In addition, the promoter remains active in the liver for a long time if it is used in adenovirus vectors with a reduced immunogenity. Thus, it may be used in a more efficient therapy of congenital gene defects of the liver.

Hereinafter the invention is explained in further detail by the following illustrative execution thereof

Example of Execution

In vivo strategies of the liver gene therapy require hepatocyte-specific vectors.

Owing to their high titre and stability in blood adenoviruses are especially suited for an in vivo gene transfer. The natural target cells for adenoviruses are cells of epithelial tissue. There is no special tropism for hepatocytes. Thus, special ways of application or modifications of the proper virus are performed for organ specificity.

The modification of virus proteins for the selective infection of hepatocytes does not appear to be promising due to the complexity of the virus coat and the virus-receptor interaction. Yet, alternatively the expression of the transferred therapeutic gene may be restricted to hepatocytes by using solely liver-specific promoters.

Cellular promoters with a known liver specificity (albumin promoters, alphal antitrypsin promoters) are not suitable for use as adenoviral vectors due to their size or are not considered for the strict metabolic control taking place (PEPCK promoter).

The hepatitis B virus has a genome of 3.2 kb, and its genes are controlled by 4 various promoters (preS1, S, core and X promoters). In addition, they are activated, to a differing degree, by 2 enhancers (enhancers I and II). All of these controlling elements comprise only a few hundred base pairs.

These promoters/enhancers were obtained from the cloned genome of the hepatitis B virus (subtype ayw) through PCR, and subsequently cloned in front of a promoterless luciferase gene. The promoters were examined for their liver specificity in a transient liver cell line test (determination of the activity of luciferase) in the liver cell lines HuH7 and HepG2 and HepSV40 and the non-liver cell lines NIH3T3, HeLa and CV1. In addition, the promoter strength was compared with that of the CMV promoter. Transfection was effected by means of the $Ca(PO_4)_2$ precipitation technique and was standardized by coprecipitation of a β-galactosidase gene controlled by a RSV promoter and measurement of the activity of β-galactosidase (FIG. 1).

Based upon these expression studies, the chosen promoter/enhancer II (pCPluc, nt 1628–1807) was the one that displayed a clear preference for hepatocytes with a moderate promoter strength.

It was assumed that the liver specificity of the expression was achieved primarily by enhancer II. In order to produce a liver-specific promoter with a higher activity, enhancer II was coupled with an enhancerless minimum promoter. The TATA box and transcription start region (nt −55−+69) of the promoter of former cytomegalovirus transcripts were used as a minimum promoter. The artificially produced promoter (EIImCMV) reaches more than 25% of the CMV promoter activity in hepatocytes, thus being classified as a strong promoter. The selectivity for hepatocytes is largely preserved. The promoter is also highly active the in primary hepatocytes of mouse, pig and man. The long-term activity in hepatocytes is decisive to the promoter's usability in gene therapy vectors. The promoter was fuised with the β-galactosidase gene and cloned in the episomal expression vector pREP8 (in vitro gene) to assess the activity. Stable hepatocyte lines (HuH7) were produced with the episome. The β-galactosidase expression was followed over the course of 3 months, and during this period a deterioration in its expression level was not detected.

In the following, the CP, EIImCMV and CMV promoters were coupled with the cDNA of the human LDL receptor.

The receptor is primarily expressed in the liver. A defective gene for the receptor serves as the basis for the hereditary disease "family hypercholesterolaemia". The disease may be treated by the purposeful transfer of an active LDL receptor gene to the liver.

The expression unit consisting of the respective promoter and the LDL receptor cDNA was inserted into the adenovirus transfer plasmid pdE1sp1A in the two possible orientations. Recombinable adenoviruses were produced by cotransfection of the adenovirus genome (pJM17) into the helper cell line HEK293. Viruses from individual recombination events were isolated by a plaque assay, reproduced in HEK293 cells, purified from cell lysate by a two-fold sedimentation in a $CsCl_2$ gradient and the titre of the virus stocks was ultimately determined.

Testing of the promoter activity and the specificity after an adenoviral gene transfer in vitro The liver cell lines HepG2 and HuH7 and the non-liver cell lines HeLa and CV1 were infected by 50 viruses/cell and the expression of the LDL receptor gene was detected three days after the infection on RNA level by RNAse protection and on protein level by Western Blot.

Figure 3:
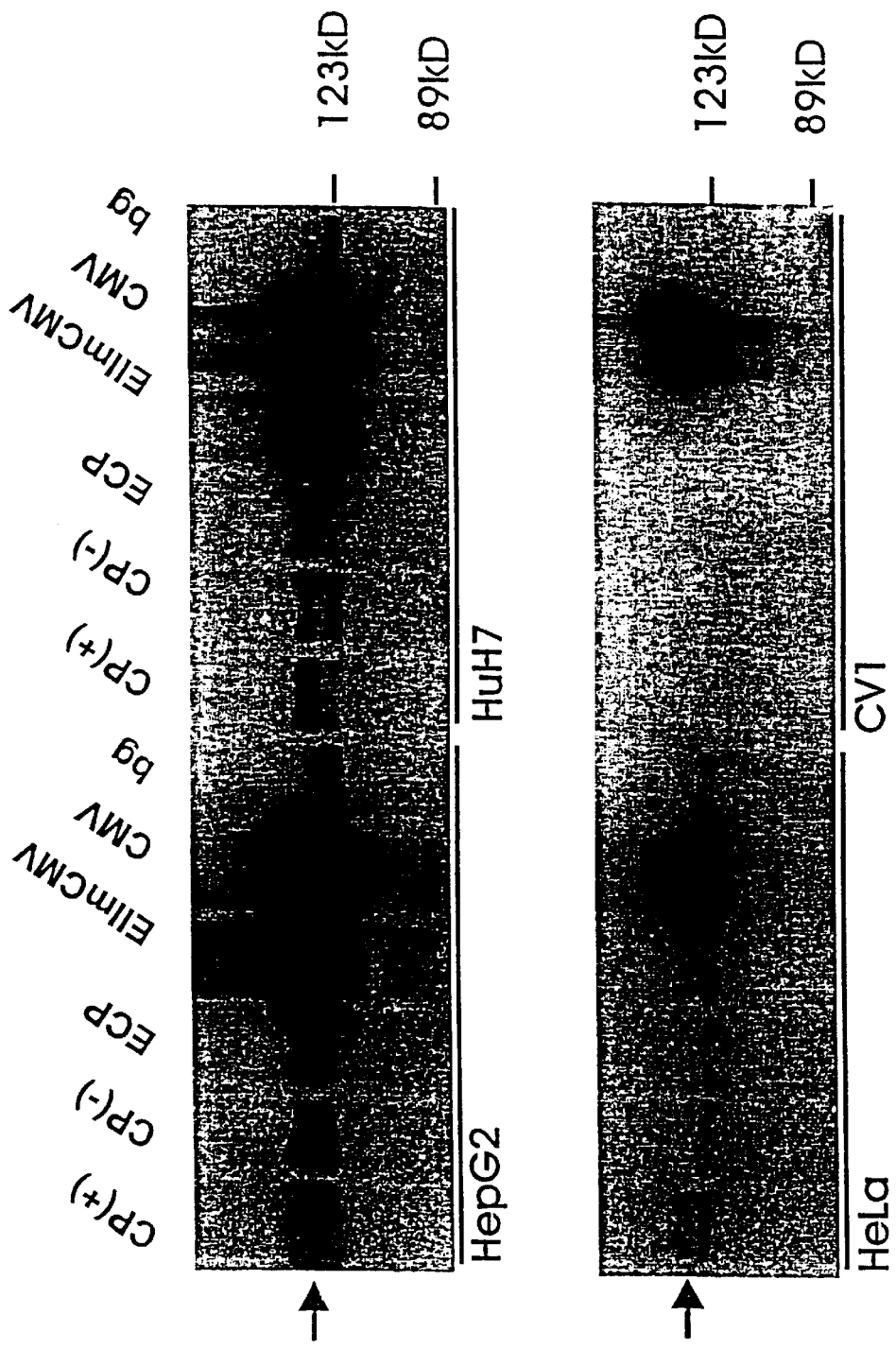
Figure 4:
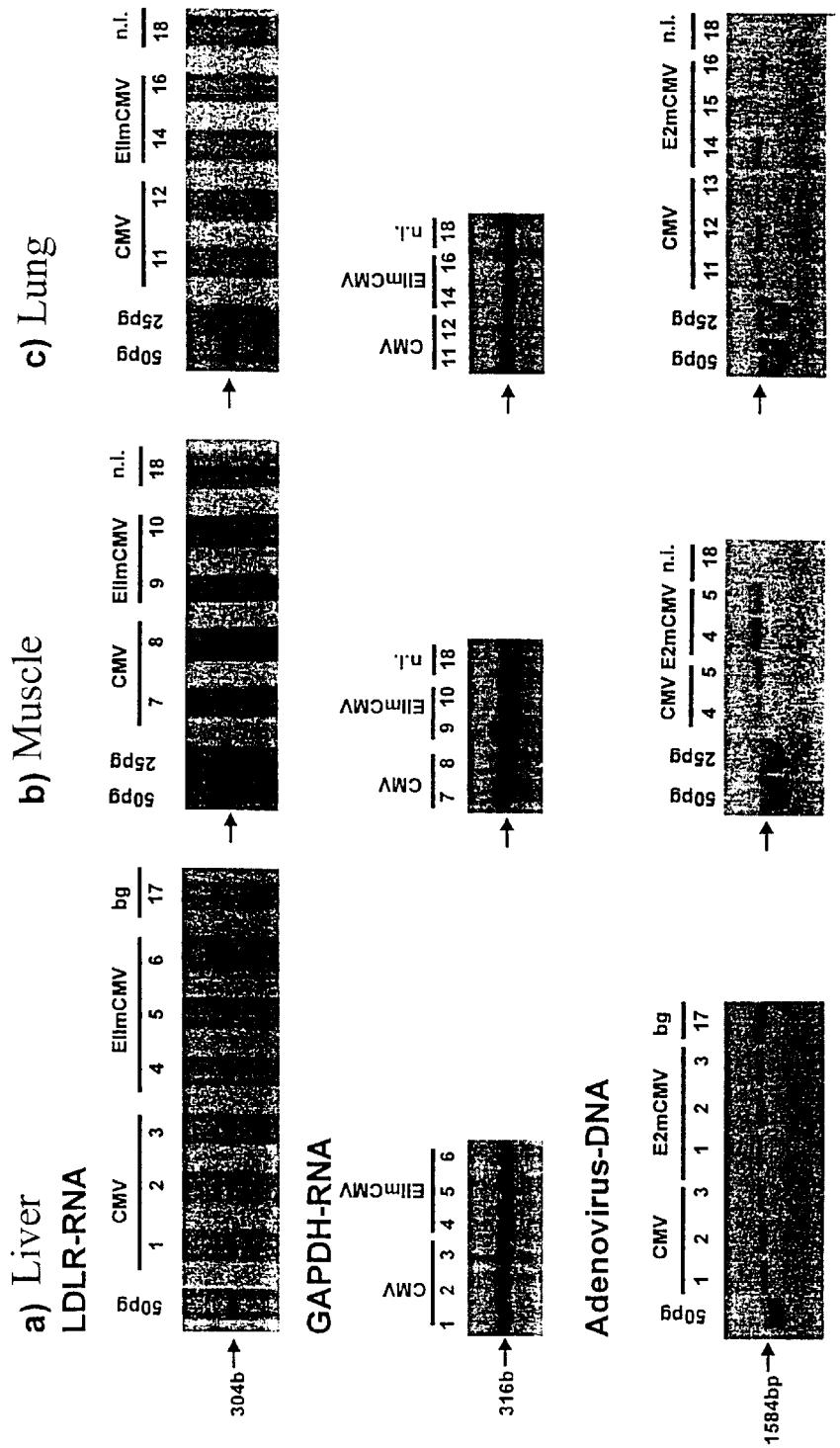

Whereas the activity of the gene controlled by the CMV promoter achieved a similar level in all examined cell lines a high expression of CP and EIImCMV promoters was only detected in hepatocyte cell lines (FIG. 3). The orientation of the expression unit in the virus has only insignificant effects on the expression level. The activity of the HBV/CMV hybrid promoter achieved approximately 30 percent of the activity of the CMV promoter.

Testing of the promoter activity and the specificity in vivo

To test the activity of the promoters in vivo, $2 \times 10^9$ adenoviruses (Ad5-CMVLDLR, Ad5-E2mCVLDLR or the controlling vector Ad5-SVbg) were always applied to the tail vein of mice (breeding race NMRI). Four days after infection the animals were killed, and the liver, lungs, diaphragm and kidney were extracted. The organs were powdered in liquid nitrogen and used for winning RNA and DNA. Southern Blot analysis has shown that an essential part of the viruses infected the liver, while in the other organs only a few viral DNA were detected. However, part of the task was to reliably detect insignificant promoter activities outside the liver. Thus, the lungs of further groups of mice were infected by intranasal application, and the viruses were injected into the muscles of a $3^{rd}$ group of animals. By using Southern Blotting techniques animals, which were detected to sustain comparable quantities of viral DNA in the infected organ, were examined for transcripts of the human LDL receptor in a "RNAse protection assay". Whereas the expression of the CMV promoter was detected in all three tissues, an expression of the EIImCMV promoter could be only detected in the liver but not in the muscles and lungs. The quality and quantity of the isolated RNA were verified for the ubiquitously active GAPDH gene by a "RNAse protection assay". As the CMV promoter showed only an insignificant activity in lungs and muscles, a highly sensitive assay was set up for competitive RT-PCR. Thereby, the same quantities of RNA from the respective organ were mixed with increasing quantities of a shortened LDL receptor RNA (competitor) which was synthesised in vitro, transcribed in reverse order and a LDL receptor fragment was amplified in a PCR. When the quantity of competitor RNA increases, the signal strength of the shortened PCR product is intensified, while an increased quantity of the longer PCR product corresponds to a decline in cellular RNA. Assuming the intensities of both bands are identical in the agarose gel, the quantity of the competitor provides information on the content of LDL receptor RNA in the tissue.

The results of competitive RT-PCR confirm those obtained by the "RNAse protection assay". The activity of the EIImCMV promoter exceeds that of the CMV promoter in the liver. Yet, in muscles and lungs it lags behind that of the CMV promoter by a factor of 10–30.

Thus, it is concluded that adenovirus vectors were constructed which allow a high expression of the LDL receptor specifically in the liver, even if the virus is administered throughout the system. Moreover, negative effects of expression in cells outside the liver are excluded.

We claim:

1. Liver-specific adenovirus expression vector comprising an adenovirus genome having inserted therein an expression unit, the expression unit comprising a therapeutic liver gene operatively coupled with a liver-specific promoter comprising enhancer elements of the hepatitis B virus and an enhancerless minimum promoter activated by said enhancer element.

2. The vector according to claim 1 wherein the expression unit is bordered in 3' and in 5' by scaffold attach region elements.

3. The vector according to claim 1, wherein said vector comprises a cDNA encoding a non-defective form of a gene associated with a disease condition.

4. The Vector according to claim 1, wherein enhancer II of the hepatitis B virus is used as one of said enhancer elements.

5. The vector according to claim 1, wherein positions 1628–1807 on the genome of the hepatitis B virus of subtype ayw are used as one of said enhancer elements.

6. The vector according to claim 1, wherein a functional portion of the immediate early promoter of the human cytomegalovirus is used as the enhancerless minimum promoter.

7. The vector according to claim 1, wherein the expression unit is inserted in the El region of the adenovirus genome.

8. The vector according to claim 3, wherein the cDNA encodes the human LDL receptor is used as the therapeutic gene.

9. The vector according to claim 6, wherein the functional portion of said cytomegalovirus promoter comprises the TATA box, the "cap site" and the 5' non-translated region.

10. The vector according to claim 7 wherein the adenovirus genome is selected from the group consisting of the adenovirus subtype 2 genome and adenovirus subtype 5 genome.

* * * * *